United States Patent
Arless et al.

[11] Patent Number: 5,899,898
[45] Date of Patent: May 4, 1999

[54] CRYOSURGICAL LINEAR ABLATION

[75] Inventors: Steven G. Arless, Beaconsfield, Canada; Fredric L. Milder, Brookline; Kenneth A. Spector, Framingham, both of Mass.; Dan Wittenberger, Montreal, Canada; Domenic N. Santoianni, St-Leonard, Canada; Claudia Lueckge, Montreal, Canada

[73] Assignee: CryoCath Technologies Inc., Quebec, Canada

[21] Appl. No.: 08/807,382

[22] Filed: Feb. 27, 1997

[51] Int. Cl.⁶ ..................................... A61B 17/36
[52] U.S. Cl. ................................. 606/22; 606/20
[58] Field of Search .................. 606/20, 22–23, 606/26

[56] References Cited

U.S. PATENT DOCUMENTS

| | | |
|---|---|---|
| 3,910,277 | 10/1975 | Zimmer . |
| 4,072,152 | 2/1978 | Linehan . |
| 4,375,220 | 3/1983 | Matvias . |
| 4,660,571 | 4/1987 | Hess et al. . |
| 4,664,120 | 5/1987 | Hess . |
| 4,690,155 | 9/1987 | Hess . |
| 4,699,147 | 10/1987 | Chilson et al. . |
| 4,709,698 | 12/1987 | Johnston et al. . |
| 4,754,752 | 7/1988 | Ginsburg et al. . |
| 4,776,349 | 10/1988 | Nashef et al. . |
| 4,945,912 | 8/1990 | Langberg . |
| 4,946,440 | 8/1990 | Hall . |
| 4,979,948 | 12/1990 | Geddes et al. . |
| 4,998,933 | 3/1991 | Eggers et al. . |
| 5,007,437 | 4/1991 | Sterzer . |
| 5,010,894 | 4/1991 | Edhag . |
| 5,100,388 | 3/1992 | Behl et al. . |
| 5,139,496 | 8/1992 | Hed . |
| 5,147,355 | 9/1992 | Friedman et al. . |
| 5,224,943 | 7/1993 | Goddard . |
| 5,228,442 | 7/1993 | Imran . |
| 5,231,995 | 8/1993 | Desai . |
| 5,281,213 | 1/1994 | Milder et al. . |
| 5,281,215 | 1/1994 | Milder et al. . |
| 5,293,869 | 3/1994 | Edwards et al. . |
| 5,325,286 | 6/1994 | Fowle ........................................ 606/23 |
| 5,334,181 | 8/1994 | Rubinsky et al. . |
| 5,403,309 | 4/1995 | Coleman et al. . |
| 5,423,807 | 6/1995 | Milder . |
| 5,452,582 | 9/1995 | Longsworth ............................. 62/51.2 |
| 5,487,385 | 1/1996 | Avitall . |
| 5,520,682 | 5/1996 | Baust et al. . |
| 5,545,200 | 8/1996 | West et al. . |
| 5,624,392 | 4/1997 | Saab .......................................... 604/43 |

*Primary Examiner*—Michael Peffley
*Assistant Examiner*—Roy Gibson
*Attorney, Agent, or Firm*—Nutter, McClennen & Fish, LLP

[57] ABSTRACT

A cryogenic catheter includes a flexible member having an elongate, thermally-transmissive region and a cryogenic fluid path through the flexible member to the thermally-transmissive region. The thermally-transmissive region can be deformable from a linear configuration to an arcuate configuration and can include multiple thermally-transmissive elements having a first side exposed to the cryogenic fluid path and a second side exposed to points exterior to the flexible member. The thermally-transmissive elements can be rigid or flexible longitudinal strips. Alternatively, annular, cylindrical, or wedge-shaped metallic structures disposed in a spaced-apart relationship can define the thermally-transmissive region. In other embodiments the thermally-transmissive region is defined by a helical coil that is at least partially embedded in the flexible member. The helical coil can also define at least a portion of the cryogenic fluid path through the flexible member and include a gas expansion or boiling chamber.

8 Claims, 5 Drawing Sheets

|  | PRESS. [psi] | TEMPERATURE [°C] | | | |
|---|---|---|---|---|---|
|  |  | TIP | RING1 | RING2 | RING3 |
| Test I |  |  |  |  |  |
|  | 230 | −45 | 6 | 16 | 13 |
|  | 250 | −45 | −36 | 3 | 1 |
|  | 270 | −43 | −43 | −19 | −20 |
|  | 290 | −40 | −47 | −23 | −22 |
|  | 310 | −40 | −47 | −32 | −25 |
|  | 330 | −39 | −47 | −38 | −27 |
|  | 350 | −39 | −47 | −47 | −31 |
|  | 370 | −40 | −47 | −48 | −45 |
|  | 390 | −39 | −47 | −48 | −49 |
|  | 410 | −36 | −46 | −47 | −49 |
|  | 430 | −36 | −46 | −48 | −49 |
|  |  |  |  |  |  |
| Test II |  |  |  |  |  |
|  | 235 | −50 |  |  |  |
|  | 275 | −51 | −52 | −4 | 6 |
|  | 300 | −44 | −50 | −53 | −2 |
|  | 325 | −43 | −51 | −52 | −24 |
|  | 350 | −43 | −50 | −51 | −33 |
|  | 375 | −42 | −49 | −50 | −52 |
|  | 400 | −40 | −49 | −50 | −53 |
|  | 425 | −39 | −48 | −49 | −51 |
|  | 449 | −37 | −47 | −48 | −50 |
|  |  |  |  |  |  |
| Test III |  |  |  |  |  |
|  | 235 | −48 | −40 | 20 | 25 |
|  | 275 | −48 | −42 | 0 | 5 |
|  | 300 | −47 | −47 | −38 | −8 |
|  | 325 | −45 | −49 | −44 | −25 |
|  | 350 | −42 | −51 | −51 | −35 |
|  | 375 | −41 | −49 | −52 | −51 |
|  | 400 | −38 | −47 | −48 | −52 |
|  | 425 | −38 | −47 | −48 | −53 |
|  | 449 | −36 | −47 | −47 | −50 |

FIG. 19

CRYOSURGICAL LINEAR ABLATION

FIELD OF THE INVENTION

The invention relates to catheters, and more particularly to cryosurgical catheters used for tissue ablation.

BACKGROUND OF THE INVENTION

Many medical procedures are performed using minimally invasive surgical techniques, wherein one or more slender implements are inserted through one or more small incisions into a patient's body. With respect to ablation, the surgical implement can include a rigid or flexible structure having an ablation device at or near its distal end that is placed adjacent to the tissue to be ablated. Radio frequency energy, microwave energy, laser energy, extreme heat, and extreme cold can be provided by the ablation device to kill the tissue.

With respect to cardiac procedures, a cardiac arrhythmia can be treated through selective ablation of cardiac tissue to eliminate the source of the arrhythmia. A popular minimally invasive procedure, radio frequency (RF) catheter ablation, includes a preliminary step of conventional electrocardiographic mapping followed by the creation of one or more ablated regions (lesions) in the cardiac tissue using RF energy. Multiple lesions are frequently required because the effectiveness of each of the proposed lesion sites cannot be predetermined due to limitations of conventional electrocardiographic mapping. Often, five lesions, and sometimes as many as twenty lesions may be required before a successful result is attained. Usually only one of the lesions is actually effective; the other lesions result in unnecessarily destroyed cardiac tissue.

Deficiencies of radio frequency ablation devices and techniques have been overcome by using cold to do zero degree or ice mapping prior to creating lesions, as taught in U.S. Pat. Nos. 5,423,807; and 5,281,213; and 5,281,215. However, even though combined cryogenic mapping and ablation devices permit greater certainty and less tissue damage than RF devices and techniques, both the cryogenic and the RF devices are configured for spot or roughly circular tissue ablation.

Spot tissue ablation is acceptable for certain procedures. However, other procedures can be more therapeutically effective if multiple spot lesions along a predetermined line, or a single elongate or linear lesion is created in a single ablative step. Radio frequency ablation devices are known to be able to create linear lesions by dragging the ablation tip along a line while it is active. However, no cryogenic devices are known that are optimized for, or which are even minimally capable of, creating an elongate lesion.

SUMMARY OF THE INVENTION

The present invention provides a cryogenic ablation system including a cryosurgical catheter that is particularly well suited for creating elongate lesions. In an exemplary embodiment, a cryogenic catheter includes a flexible member having an elongate, thermally-transmissive region and a cryogenic fluid path through the flexible member to the thermally-transmissive region. The thermally-transmissive region can be deformable from a linear configuration to an arcuate configuration and can include multiple, thermally-transmissive elements having a first side exposed to the cryogenic fluid path and a second side exposed to points exterior to the flexible member.

The thermally-transmissive elements can be rigid or flexible longitudinal strips. Alternatively, rigid or flexible annular, cylindrical, or wedge-shaped metallic structures disposed in a spaced-apart relationship can define the thermally-transmissive region. The thermally-transmissive elements can define continuous 360 degree structures or arcuate structures that are less than 360 degrees and/or which do not fully traverse the circumference of the catheter.

In other embodiments, the thermally-transmissive region is defined by a helical coil that is at least partially embedded in the flexible member. The helical coil can also define at least a portion of the cryogenic fluid path through the flexible member and can include a gas expansion or boiling chamber.

The cryogenic catheter of the invention can be a component in a cryogenic system that further includes a cryogenic fluid supply in communication with the cryogenic catheter, and a fluid controller interposed between the cryogenic catheter and the cryogenic fluid supply for regulating the flow of the cryogenic fluid into the cryogenic catheter. The cryogenic fluid can be a gas or a liquid.

The present invention further includes a method of making an elongate lesion, wherein cryogenic temperatures are sequentially achieved along a thermally-transmissive region over a predetermined time interval.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 19 is a table illustrating cooling performance of a catheter in accordance with the invention.

DETAILED DESCRIPTION OF THE INVENTION

Figure 1:
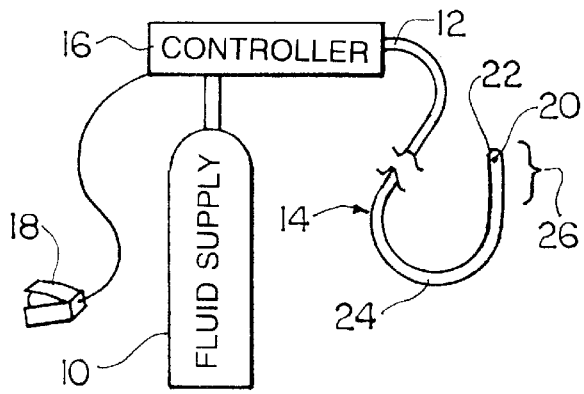
FIG. 1 is a schematic illustration of an embodiment of a cryosurgical system in accordance with the invention.

FIG. 1 is a schematic illustration of a cryosurgical system in accordance with the invention. The system includes a supply of cryogenic or cooling fluid 10 in communication with the proximal end 12 of a flexible catheter 14. A fluid controller 16 is interposed or in-line between the cryogenic fluid supply 10 and the catheter 14 for regulating the flow of cryogenic fuid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals. In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example a temperature sensor can be placed at a point proximate the distal end 22 of the catheter and other temperature sensors 20 can be placed at spaced intervals between the distal end of the catheter and another point that is between the distal end and the proximal end.

The cryogenic fluid can be in a liquid or a gas state. An extremely low temperature can be achieved within the catheter, and more particularly on the surface of the catheter by cooling the fluid to a predetermined temperature prior to its introduction into the catheter, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50—50 mixture of difluoromethane & pentafluoroethane sold by Allied Signal), and CFC's such as DuPont's Freon. Exemplary gasses include nitrous oxide, and carbon dioxide.

The catheter 14 includes a flexible member 24 having a thermally-transmissive region 26 and a fluid path through the flexible member to the thermally-transmissive region. A fluid path is also provided from the thermally-transmissive region to a point external to the catheter, such as the proximal end 12. Although described in greater detail below, exemplary fluid paths can be one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat.

For example, a metal structure exposed (directly or indirectly) to the cryogenic fluid path is considered a thermally-transmissive region 26 even if an adjacent polymeric or latex catheter portion also permits heat transfer, but to a much lesser extent than the metal. Thus, the thermally-transmissive region 26 can be viewed as a relative term to compare the heat transfer characteristics of different catheter regions or structures.

Furthermore, while the thermally-transmissive region 26 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process without having to relocate the catheter one or more times or drag it across tissue. Additional details of the thermally-transmissive region 26 and the thermal transfer process are described in greater detail below.

In exemplary embodiments of the invention, the thermally-transmissive region 26 of the catheter 14 is deformable. An exemplary deformation is from a linear configuration to an arcuate configuration and is accomplished using mechanical and/or electrical devices known to those skilled in the art. For example, a wall portion of the flexible member 24 can include a metal braid to make the catheter torqueable for overall catheter steering and placement. Additionally, a cord, wire or cable can be incorporated with, or inserted into, the catheter for deformation of the thermally transmissive region 26.

Figure 2:
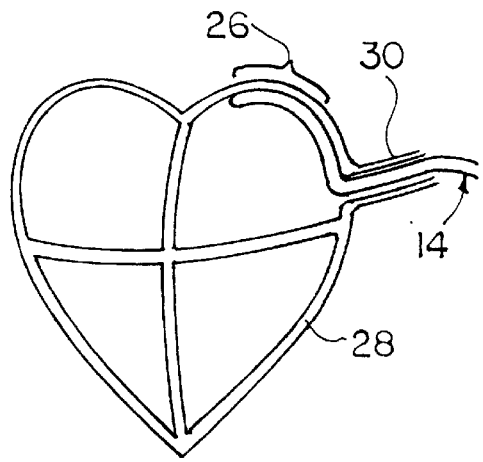
FIG. 2 is a sectional view of a heart muscle showing placement of the catheter of FIG. 1.

The cryogenic system of FIG. 1 is better understood with reference to its use in an operative procedure as shown in FIG. 2. Following the determination of a proposed lesion site within a heart muscle 28 for example, the catheter 14 is directed through a blood vessel 30 to a region within the heart, such as an auricle, where the lesion will be made. The thermally-transmissive region 26 is placed proximate to the tissue to be ablated. The thermally-transmissive region of the catheter may be deformed to conform to the curvature of the tissue before, during, or after placement against the tissue. The controller 16 allows or causes cryogenic fluid to flow from the cryogenic fluid supply 10 to the fluid path in the catheter 14 and thence to the thermally-transmissive region 26 to ablate the desired area or to cold map along the same tissue area. In one embodiment (e.g., FIG. 12) a first conduit is concentric within a second conduit and cooling fluid travels to a thermally-transmissive region proximate a closed distal end of the catheter through a first conduit (fluid path) and is exhausted from the catheter through the second conduit (fluid path).

Having described the function of the cryogenic catheter 14 and its use in a system context, several exemplary embodiments of the thermally-transmissive region 26 of the catheter are now described in greater detail. FIGS. 3, 4, 5, 12–16 and 18 illustrate embodiments of the catheter, or portions thereof, having two or more thermally-transmissive segments in a spaced-apart relationship. Each of the illustrated catheters includes a closed tip 32 that can include a thermally-transmissive material.

Figure 3:
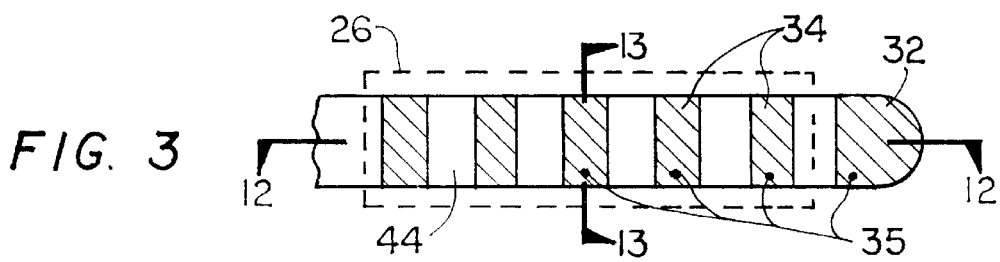
FIG. 3 illustrates the tip region of one embodiment of the catheter in accordance with the invention.
Figure 13:
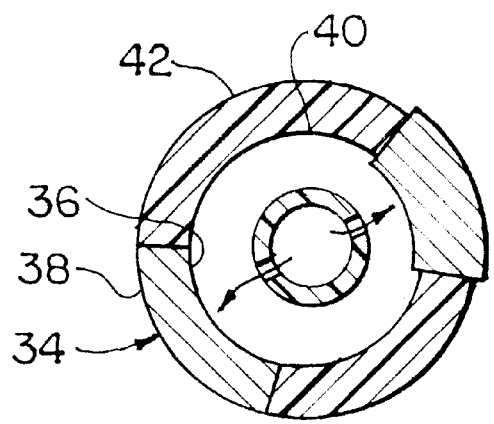
FIG. 13 is a sectional view of the catheter of FIG. 3 taken along line 13—13.
Figure 14:
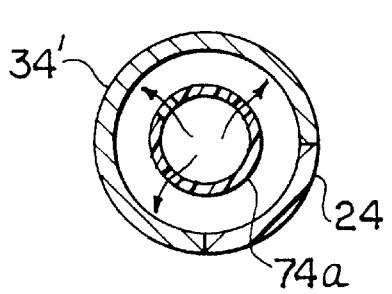
FIGS. 14–16 are sectional views of additional catheter embodiments.
Figure 15:
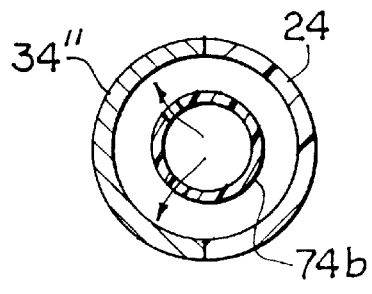
Figure 16:
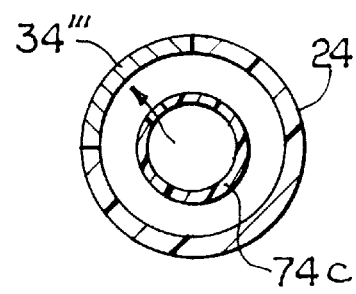

Referring specifically to the embodiment depicted in FIG. 3, multiple thermally-transmissive elements 34 are integral with a distal portion of a catheter. Each of the thermally-transmissive elements 34 includes a first side or face 36 (shown in FIGS. 12 and 13) exposed to a cryogenic fluid path and cryogenic fluid (shown by arrows) and a second side or face 38 exposed to points exterior to the catheter. As shown in FIG. 13, the first side 36 and/or second side 38 of any or all of the thermally-transmissive elements 34 can be substantially flush with, recessed below, or protruding from the inner surface 40 and outer surface 42 of a portion of the catheter. The thermally-transmissive elements 34 are separated by flexible portions of material 44 than can range from slightly less thermally-transmissive than the adjacent thermally-transmissive elements to substantially less thermally-transmissive than the adjacent elements. In the illustrated embodiment of FIG. 3, the thermally-transmissive elements 34 are annular, cylindrical elements which are made of gold-plated copper or bronze. Thermocouples 35 can be associated with one or more of the elements 34 and the tip 32. The thermally-transmissive elements 34 can be completely exposed, embedded, or a combination thereof along the full 360° of the catheter's circumference. In certain applications the thermally-transmissive elements traverse or define less than 360° of the catheter's circumference as shown in FIGS. 14–16 and as described below. The longitudinal width of each thermally-transmissive element 34, the spacing between elements, the material thickness, and the material composition are matched with a selected cooling fluid and fluid delivery pressure to produce overlapping cold regions which produce a linear lesion.

Figure 4:
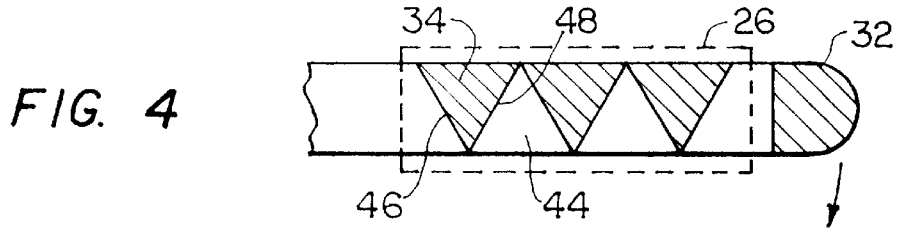
FIG. 4 illustrates an alternative embodiment of the catheter of FIG. 3.

The embodiment illustrated in FIG. 4 is substantially identical to the embodiment of FIG. 3, however, at least one of the thermally-transmissive elements 34 includes a first open end 46 that defines a first plane and a second open end 48 that defines a second plane, wherein the first and second planes intersect to give the annular elements a wedge-like appearance. Such a configuration permits adjacent thermally-transmissive elements 34 to be positioned very closely together, but it can limit the possibilities for deforming the thermally-transmissive region 26, which, in this embodiment, is flexible in the direction indicated by the arrow.

Figure 5:
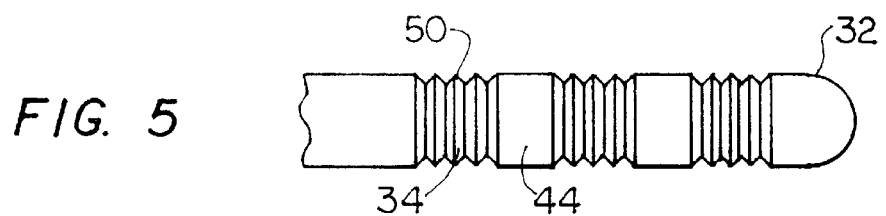
FIG. 5 illustrates yet another embodiment of the catheter.

With respect to the embodiments shown in both FIGS. 3 and 4, the thermally-transmissive elements 34 are substantially rigid and are separated and/or joined by a flexible material 44. However, in other embodiments the thermally-transmissive elements 34 are flexible and are interdigitated with either rigid or flexible segments. FIG. 5, for example, illustrates an embodimet of the cryogenic catheter having three thermally-transmissive elements 34 that are flexible. The flexibility is provided by a folded or bellows-like structure 50. In addition to being shapable, a metal bellows can have enough stiffness to retain a selected shape after a deforming or bending step.

Figure 6:
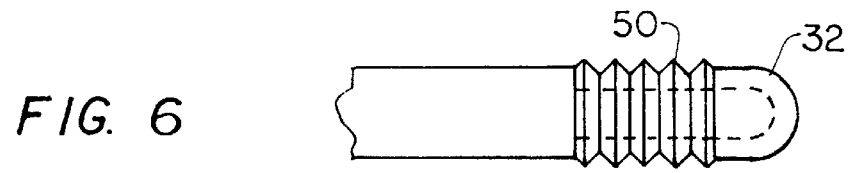
FIG. 6 illustrates a deformable tip for a catheter.

Instead of, or in addition to, flexible, thermally-transmissive elements 34 and/or flexible material 44 between elements, the distal tip 32 (or a portion thereof) can be deformable. For example, FIG. 6 illustrates a tip 32 having thermally-transmissive, flexible, bellows 50.

Figure 7:
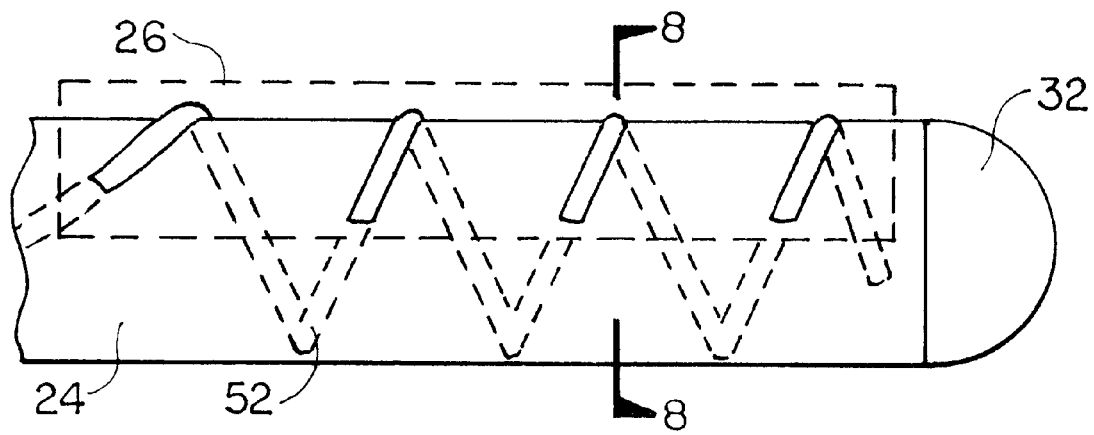
FIG. 7 illustrates yet another embodiment of the catheter.
Figure 8:
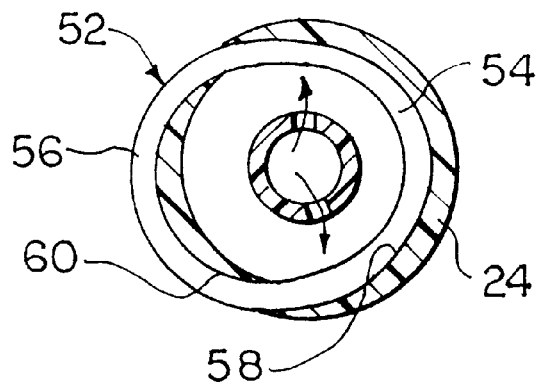
FIG. 8 is a sectional view of the catheter of FIG. 7 taken along line 8—8.

Referring now to FIGS. 7–10, a different approach is shown for providing multiple thermally-transmissive segments in a spaced-apart relationship. FIG. 7 illustrates a catheter embodiment having an elongate, thermally-transmissive region 26 that includes a helical coil 52 at least partially embedded in the flexible member 24. As shown in FIG. 8, at least a first portion 54 of the helical coil 52 is exposed to a fluid path within the flexible member 24 and a second portion 56 of the helical coil is exposed to the exterior of the flexible member. As described above with respect to FIG. 13, the first portion 54 of the coil can be substantially flush with, recessed below, or protruding from an inner surface 58 of the flexible member 24. Similarly, the second portion 56 of the coil 52 can be substantially flush with, recessed below, or protruding from an outer surface 60 of the flexible member 24.

In the embodiment of FIG. 8, the second portion 56 of the coil 52 is exposed along only a portion of the outer circumference of the flexible member 24 to define a longitudinally-elongate, thermally-transmissive region 26. This configuration can be provided by eccentrically mating the helical coil 52 to the catheter so that the longitudinal axis of the coil and the longitudinal axis of the catheter are substantially parallel. The eccentric positioning of the coil 52 provides excellent cooling performance because the surface area available for thermal exchange between the first portion 54 of coil and the cryogenic fluid is greater than the surface area available for thermal exchange between the second portion 56 of the coil and adjacent tissue where cooling power is delivered by each exposed coil portion to provide a linear lesion.

Figure 9:
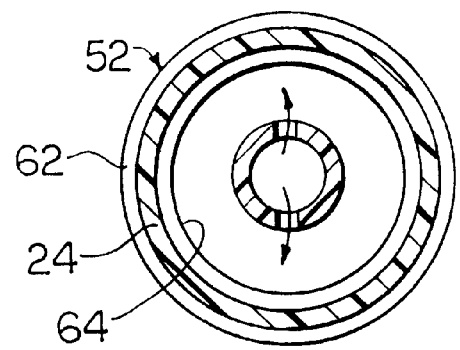
FIG. 9 is a sectional view of an alternative embodiment of the linear ablation catheter illustrated in FIG. 7.

Referring now to FIG. 9, an alternative embodiment is shown wherein a first portion 62 of the coil 52 is exposed around the entire circumference of the flexible member 24, and a second portion 64 is exposed to a fluid path around the inner surface of the flexible member 24. This is achieved by having the longitudinal axis of the helical coil 52 co-axial with the longitudinal axis of the catheter.

Figure 10:
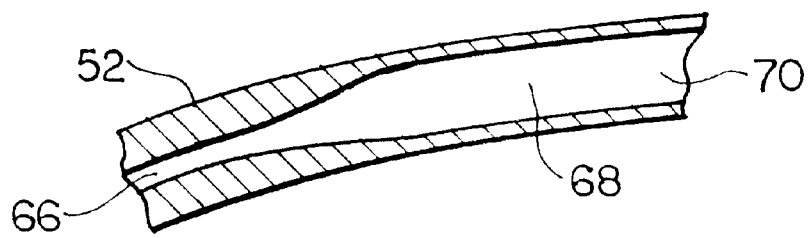
FIG. 10 illustrates an expansion chamber within a portion of a helical coil.

In the embodiments illustrated in FIGS. 7–9, the coil 52 is solid. However, in other embodiments the coil can be an elongate, hollow, gas expansion chamber. For example, FIG. 10 illustrates a portion of a helical coil 52 that includes a passage that defines at least a portion of a fluid path through a flexible member of the catheter. The coil 52 defines a first fluid path diameter at a fluid entry point 66 and a second fluid path diameter that is greater than the first fluid path diameter at a gas expansion or boiling location 68. Gas escaping from a fluid exit point 70 can be exhausted through an open central region of the coil and/or another passage through the flexible member 24.

Figure 11:
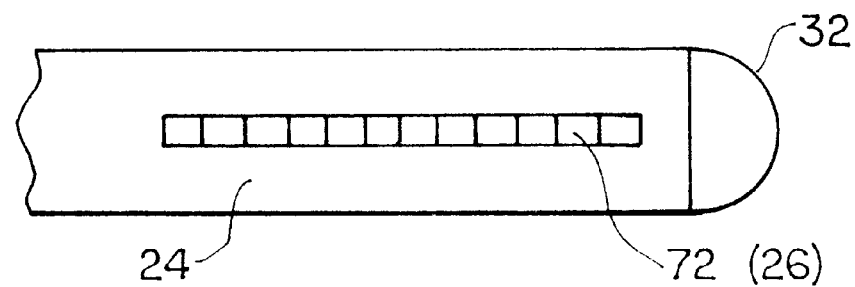
FIG. 11 illustrates a portion of a catheter having an elongate, thermally-transmissive strip.

FIG. 11 illustrates an embodiment of the catheter wherein a continuous, elongate, thermally-transmissive strip 72 is longitudinally integrated with a flexible member 24. The strip can include a bellows-like structure. As described above with respect to other embodiments, a first portion of the strip can be substantially flush with, recessed below, or protrude from the outer surface of the flexible member. Similarly, a second portion of the strip can be substantially flush with, recessed below, or protrude from an inner surface of the flexible member.

Figure 12:
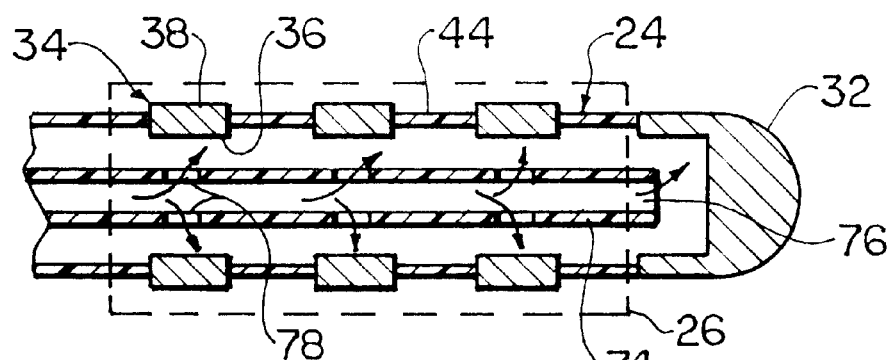
FIG. 12 is a sectional view of the catheter of FIG. 3 taken along line 12—12.

Referring now to FIG. 12, an embodiment of the catheter is illustrated having a second or inner flexible member 74 concentric within a first or outer flexible member 24, wherein the second flexible member defines a fluid path to the thermally-transmissive region 26. The inner member 74 can include a single opening 76 at or near the tip 32. Cryogenic fluid is expelled from the opening 76 and returns to the proximal end of the catheter along a fluid path defined by the outer wall of the inner member 74 and the inner wall of the outer member 24. This fluid path configuration is also partially illustrated in FIGS. 8, 9, and 13. Alternatively, as also shown in FIG. 12, the inner member 74 can be provided with multiple openings 78 proximate to and/or aligned with the inner face of one or more thermally-transmissive elements 34 to achieve more uniform cooling across the entire elongate, thermally-transmissive region 26.

Referring now to FIGS. 14–16, sectional views of catheter embodiments are illustrated to show alternative configurations for thermally-transmissive elements. The previously described thermally-transmissive elements 34 are arcuate and form complete and continuous 360 degree structures that traverse the complete circumference of the catheter, notwithstanding being flush with, depressed below, or raised above the outermost surface of the flexible member 24. However, the arcuate elements 34', 34", and 34'" illustrated in FIGS. 14–16, respectively, traverse less than 360 degrees of the circumference of the first flexible member and do not form complete loops. For example, in FIG. 14, element 34' defines an approximately 270 degree arc. In FIG. 15 the thermally-transmissive element 34" defines an approximately 180 degree arc; and in FIG. 16, the thermally-transmissive element 34'" defines an approximately 90 degree arc. A catheter can include combinations of element types, such a complete ring or loop element a 270 degree element and a 180 degree element as desired to define a thermally transmissive region. In addition to the having applicability with respect to rigid thermally-transmissive elements, the bellows-like elements can also be less than 360 degrees.

The less than 360 degree arcuate elements provide unique functional benefits with respect to thermal transfer and flexibility of the thermally-transmissive region. For example, because the portion of the catheter between the opposing ends of element 34', 34'', 34''' does not include a rigid structure, but rather only the resilient material of flexible member 24, the thermally-transmissive region of the catheter can be more tightly curved (gap between ends inward and element facing outward) than it could with complete 360 degree structures, especially if the elements are relatively long longitudinally.

The inner member 74 can be adapted to direct cooling fluid at only the thermally-transmissive element(s) and the shape and/or the number of openings for cooling fluid can be configured differently depending on the length of the arc defined by the thermally-transmissive element(s). For example, FIG. 14 illustrates an embodiment of the inner member having three openings opposing the thermally transmissive element 34'; FIG. 15 illustrates two openings for a smaller arc; and FIG. 16 discloses a single opening for an even smaller arc.

Another advantage to providing one or more thermally-transmissive elements that have a less than 360 degree configuration is that limiting the span of the elements to a desired lesion width, or somewhat greater than a desired lesion width, reduces the thermal load on the system and/or permits colder temperatures to be achieved than with respect to a complete 360 degree structure. Unnecessary and perhaps undesirable cooling does not occur at any other location along the catheter except at an elongate region of predetermined width. A similar effect can also be achieved by providing a non-circular 360 degree element or by eccentrically mounting a circular 360 degree element with respect to the flexible member, wherein a portion of the 360 degree element is embedded within the wall of the flexible member or otherwise insulated from the cryogenic fluid path in a manner similar to that shown in FIG. 8.

Figure 17:
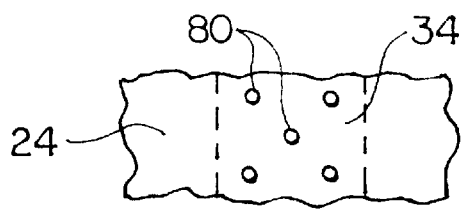
FIG. 17 illustrates an inner face of a flexible catheter member.

Referring now to FIG. 17, a portion of the inner face of an outer flexible member showing thermal transfer pins 80 protruding from the inner face of a thermally-transmissive element 34. The pins permit thermal transfer through the flexible member 24. As with the other features of the invention, the pins are equally suitable for complete 360 degree element structures or less than 360 degree structures.

Figure 18:
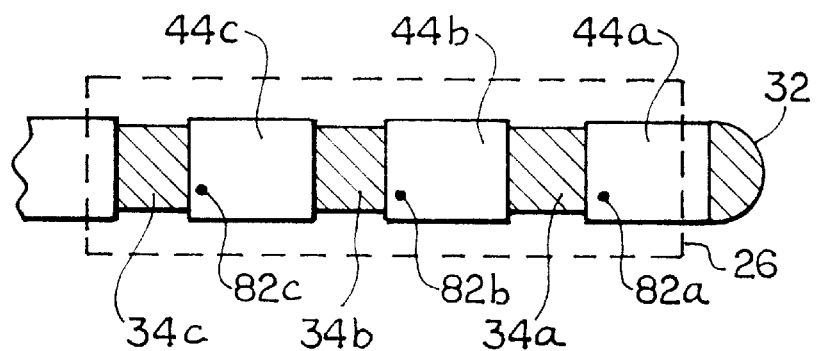
FIG. 18 depicts yet another embodiment of a catheter in accordance with the invention.

Referring now to FIG. 18, yet another embodiment of the catheter is shown wherein rigid metal rings 34a–c are interdigitated with flexible segments 44a–c to define a first flexible member and a thermally-transmissive region approximately one inch in length. A second flexible member is concentric within the first flexible member and has an outlet for cryogenic fluid at its distal end. Thermocouples 82a–c can be associated with one or more of the rings 34a–c.

It has been described above how the thermal loading of a cooling system can be reduced by providing thermally-transmissive elements that span less than 360 degrees. However, the thermal loading can also be reduced by sequentially cooling the tip and rings that comprise the thermally-transmissive region. One way to sequentially cool the tip and rings is to modulate the pressure of the cooling fluid along the fluid path through the flexible member. This modulation can be performed by the fluid controller which can be programmed to increase and decrease the pressure of the fluid by predetermined pressure increments over predetermined time intervals. When the cryogenic fluid is a liquid that provides cooling by changing phase from liquid to gas, the change of pressure alters the physical location along the fluid path where the phase change takes place and concomitantly changes the point of coldest temperature along the thermally-transmissive region. Thus, varying the pressure of the fluid can provide a moving ice-formation "front" along the catheter, enabling the creation of a linear lesion.

Therefore, a method of forming an elongate tissue lesion can include the following steps using any of the above described catheters having an elongate, thermally-transmissive region. In a first step a cryogenic fluid is introduced into the flexible member at a first predetermined pressure. Next, the pressure of the cryogenic fluid is incrementally increased within the flexible member until a second predetermined pressure is achieved. Similarly, the pressure of the cryogenic fluid within the flexible member can be decreased incrementally from the second predetermined pressure to the first predetermined pressure, wherein the steps of incrementally increasing and decreasing the pressure define a thermal cycle. Typically, from one to eight thermal cycles are required to achieve a desired therapeutic effect. In an exemplary method, about ten increments of about five seconds in duration are selected and pressure is increased by about 20 to 40 pounds per square inch in each increment. Thus, using this method an elongate lesion can be created in less than 20 minutes.

FIG. 19 is a table that illustrates sequential cooling in a catheter as described above having a thermally-transmissive region that includes a tip and three elements or rings. The table illustrates three tests conducted in a still bath at 37° C., using AZ-20 as the cryogenic fluid. Associated with each pressure increment are measured temperatures at the tip, first ring, second ring, and third ring. The shaded region illustrates the sequential movement of a target temperature range (upper –40's to low –50's) in response to a change in pressure. Although values are only provided for three rings, a similar effect and pattern is obtained with more than three rings or elements.

A variety of modifications and variations of the present invention are possible in light of the above teachings. It is therefore understood that, within the scope of the appended claims, the present invention may be practiced otherwise than as specifically described hereinabove. All references cited herein are expressly incorporated by reference in their entirety.

What is claimed is:

1. A cryogenic catheter comprising:
   a flexible member having an elongate, elastic, thermally-transmissive region; and
   a cryogenic fluid path through the flexible member to the thermally-transmissive region,
   wherein the elongate, thermally-transmissive region includes a helical coil that is at least partially embedded in the thermally-transmissive region.

2. The cryogenic catheter of claim 1, wherein the thermally-transmissive region is steerable.

3. The cryogenic catheter of claim 2, wherein the thermally-transmissive region is elastically deformable from a linear configuration to an arcuate configuration.

4. The cryogenic catheter of claim 1, wherein the flexible member and the helical coil each have a longitudinal axis and wherein the respective longitudinal axes are co-axial.

5. The cryogenic catheter of claim 1, wherein the helical coil includes a passage that defines at least a portion of the cryogenic fluid path through the flexible member.

6. The cryogenic catheter of claim 5, wherein the helical coil includes a cryogenic fluid entry point leading to an expansion location within the helical coil.

7. A cryogenic catheter comprising:

a flexible member having an elongate, thermally-transmissive region; and a cryogenic fluid path through the flexible member to the thermally-transmissive region, wherein the elongate, thermally-transmissive region includes a helical coil that is at least partially embedded in the flexible member, and wherein at least a first portion of the helical coil is exposed to the cryogenic fluid path and a second portion of the helical coil is exposed to points exterior to the flexible member.

8. A cryogenic catheter comprising:

a flexible member having an elongate, thermally-transmissive region; and a cryogenic fluid path through the flexible member to the thermally-transmissive region, wherein the elongate, thermally-transmissive region includes a helical coil that is at least partially embedded in the flexible member, and wherein the flexible member and the helical coil each have a longitudinal axis and wherein the respective longitudinal axes are not co-axial.

* * * * *